United States Patent
Lee et al.

[19]
[11] Patent Number: 6,122,542
[45] Date of Patent: Sep. 19, 2000

[54] BREAST STABILIZATION DEVICES AND IMAGING AND INTERVENTIONAL METHODS USING THE SAME

[75] Inventors: Roberta Lee, Redwood City; James W. Vetter, Portola Valley; Natalie N. Hyland, Redwood City, all of Calif.

[73] Assignee: Rubicor Medical, Inc., Redwood City, Calif.

[21] Appl. No.: 09/200,661

[22] Filed: Nov. 25, 1998

[51] Int. Cl.[7] .................................................. A61B 5/05
[52] U.S. Cl. .................... 600/427; 600/437; 600/439; 128/915; 378/37
[58] Field of Search .................................. 600/427, 437, 600/439, 407, 473, 476; 128/915; 378/37, 62, 63

[56] References Cited

U.S. PATENT DOCUMENTS

| | | |
|---|---|---|
| 3,971,950 | 7/1976 | Evans et al. . |
| 4,434,799 | 3/1984 | Taenzer .................... 600/448 |
| 4,509,368 | 4/1985 | Whiting et al. ............. 73/624 |
| 4,563,768 | 1/1986 | Read et al. . |
| 4,691,333 | 9/1987 | Gabriele et al. . |
| 4,829,184 | 5/1989 | Nelson et al. ............ 250/358.1 |
| 5,009,660 | 4/1991 | Clapham . |
| 5,056,523 | 10/1991 | Hotchkiss, Jr. et al. ....... 128/653.1 |
| 5,171,321 | 12/1992 | Davis . |
| 5,308,321 | 5/1994 | Castro . |
| 5,386,447 | 1/1995 | Siczek ........................ 378/37 |
| 5,409,497 | 4/1995 | Siczek et al. ............. 128/653.1 |
| 5,451,789 | 9/1995 | Wong et al. ............. 250/363.03 |
| 5,590,166 | 12/1996 | Suni et al. ................... 378/37 |
| 5,590,655 | 1/1997 | Hussman . |
| 5,660,185 | 8/1997 | Shmulewitz et al. ............ 128/749 |
| 5,662,109 | 9/1997 | Hutson ................... 128/653.1 |
| 5,702,405 | 12/1997 | Heywang-Koebrunner . |
| 5,706,327 | 1/1998 | Adamkowski et al. ........... 378/37 |
| 5,776,177 | 7/1998 | MacWhinnie et al. . |
| 5,805,665 | 9/1998 | Nelson et al. ............... 378/207 |
| 5,810,742 | 9/1998 | Pearlman . |
| 5,820,552 | 10/1998 | Crosby et al. .............. 600/407 |
| 5,855,554 | 1/1999 | Schneider et al. ............ 600/407 |
| 5,860,934 | 1/1999 | Sarvazyan ................. 600/587 |
| 5,868,673 | 2/1999 | Vesely .................... 600/407 |
| 5,876,339 | 3/1999 | Lemire ................... 600/425 |
| 5,899,865 | 5/1999 | Chance ................... 600/473 |
| 5,999,836 | 12/1999 | Nelson et al. .............. 600/407 |

FOREIGN PATENT DOCUMENTS

| | | |
|---|---|---|
| 26 10 111 | 9/1977 | Germany . |
| WO 99/08647 | 2/1999 | WIPO . |

OTHER PUBLICATIONS

NeoVision Corporation: SONOPSY Ultrasound–Guided Breast Biopsy: Document No. 10369, Revision 1, Oct. 1996.

*Primary Examiner*—Teresa Walberg
*Assistant Examiner*—Jeffrey Pwu
*Attorney, Agent, or Firm*—Young Law Firm. P.C.

[57] ABSTRACT

A breast stabilization device for imaging and invasive medical procedures includes a shell configured to surround a superior portion of a breast when the breast rests on a substantially flat surface. The shell includes a first opening configured to allow at least a portion of a nipple-areolar complex of the breast to protrude therethrough. A first and second flange extend from the shell to secure the shell to the flat surface. A third flange may also be included to secure the shell to the patient's chest wall. The shell includes a substantially rigid outer member and a relatively softer inner member that is in contact with the patient's breast when the device is in use. The substantially rigid outer member includes a suction port and the relatively softer inner member includes a through holes in fluid communication with the suction port, to allow a patient's breast to be drawn toward the inner member when fluid is drawn from the suction port. Imaging and interventional procedures may be carried out through the opening by making an incision in the superior portion of the peri-areolar border. Both surface and intra-tissue ultrasound may be utilized to localize the lesion and to provide real time imaging of the uncompressed and stabilized breast during the breast-stabilized biopsy or excisional procedure.

22 Claims, 5 Drawing Sheets

BREAST STABILIZATION DEVICES AND IMAGING AND INTERVENTIONAL METHODS USING THE SAME

BACKGROUND OF THE INVENTION

1. Field of the Invention

The present invention pertains to the field of diagnostic and therapeutic medical devices and procedures. More particularly, the present invention relates to the field of stabilization, imaging and procedure facilitating platforms for the female breast.

2. Description of the Related Art

Women aged 40 and over are recommended to undergo an annual screening mammogram to potentially identify a breast cancer in its most early stages of development. By definition, these women are asymptomatic and the lesions within their breasts, if any, are most often non-palpable. Most small breast cancers are, therefore, diagnosed by screening mammography. To obtain an acceptable mammographic image, the breast must be compressed and held immobile between two parallel plates. Compression is mandatory to obtain the required mammographic views, as an adequate mammogram cannot be obtained unless the breast is in compression. Conventionally, a computer calculates the x, y and z coordinates targeting the lesion and a biopsy instrument is then inserted within the compressed breast to biopsy the lesion.

Because of the required compression, the placement of the compression plates on the woman's breast determines the skin entry site for the procedure and, therefore, the location of the resulting scar. Indeed, the position of the breast in the compression device dictates where the incision is to be made. Conventionally, the scar is most always on the side of the breast, whether superior, lateral, inferior or medial. The scar can range from about 5 mm in length to an unsightly 3 cm if a large coring device is used.

Examples of such devices and methods include that disclosed in U.S. Pat. No. 5,702,405 issued Dec. 30, 1997 to Heywang-Koebrunner. As described in this reference, the breast is compressed between two plates of a stereotactic attachment to a tomography device. Through holes are disposed in one of the two compression plates at an oblique angle within a plane that is substantially perpendicular to the plane of the plates, to allow a biopsy needle to access the breast through the side thereof. Similarly, U.S. Pat. No. 4,563,768 to Read et al. discloses a mammographic device utilizing two parallel plates to compress the breast. One of the compression plates functions as an X-ray film holder. A matrix of perforations is disposed in one the compression plates, allowing access to the side of the breast by a biopsy needle or the like. U.S. Pat. No. 4,691,333 uses similar breast compression and side access technology. LaBash, in U.S. Pat. No. 5,499,989 discloses yet another breast compression scheme, in which the breast is stabilized by compression, whereupon a guide spool is aligned over an opening in one of the plates. The guide spool guides a tubular punch or a biopsy needle through the breast to the lesion site, puncturing the side of the compressed breast.

These and other similar devices share a number of disadvantages. When the lesion is biopsied with the breast in compression, the cavity left after the biopsy procedure expands as the breast is uncompressed after the procedure. This expanded cavity can cause unsightly disfigurements, particularly when large coring devices are used. It would be advantageous, therefore, to perform the biopsy procedure on an uncompressed breast. However, localization of small breast lesions has conventionally required mammographic imaging. Mammographic imaging, in turn, requires that the breast remain compressed.

Ultrasound imaging is currently used with good results for specific indications, but is generally not used as a screening modality. Indeed, ultrasound is conventionally used to gather additional information about a suspicious area seen on mammography, or about a palpable lesion. Conventionally, it has been difficult to determine conclusively that a suspicious area as seen by ultrasound correlates exactly with that seen during the mammogram. In addition, suspicious microcalcifications seen by mammography are not readily visualized by ultrasound imaging techniques currently available. Therefore, ultrasound conventionally has been of little help in biopsying or excising small, non-palpable cancers or suspicious areas.

In instances where surface ultrasound is effective in localizing a lesion, a manual biopsy procedure may be carried out under surface ultrasonic guidance. In such a directed biopsy procedure, the lesion within the breast is sonographically targeted and a fine needle aspiration, core biopsy or vacuum-assisted core biopsy procedure is carried out. In such a procedure, the breast is not compressed and a surface ultrasound transducer is typically used to image the breast and the site of interest therein. In surface ultrasound-guided biopsy, the physician must manually (i.e., by placing a hand on the breast) stabilize the breast as best as possible, hold the ultrasound probe, and perform the biopsy accurately enough to obtain tissue from the lesion. Conventionally, this procedure is carried out by inserting the needle within the breast in an orientation that is as near parallel to the patient's chest wall as possible. The breast stabilization, the operation of the probe, as well as the actual needle biopsy must be carried out simultaneously, all the while maintaining the needle within the focal plane of the ultrasound probe. It is difficult to have an assistant help perform the procedure because if the ultrasound probe and/or needle are not exactly in line and are off by a fraction of a millimeter, then the needle cannot be visualized on the ultrasound monitor. Moreover, any movement of the patient (e.g., coughing, shifting) will also cause the biopsy device and surface ultrasound probe to misalign.

Carrying out biopsy procedures on the uncompressed breast would alleviate the disadvantages associated with compressing the breast. Importantly, such procedures on the uncompressed breast would be less painful, would allow more choices for the entry site, would reduce the size of the cavity left after the excisional procedure and would provide a means for excising tissue from the breast in its natural state.

SUMMARY OF THE INVENTION

In accordance with the principles of the present invention, a breast stabilization device for imaging and invasive medical procedures comprises:

a shell configured to surround a portion of a breast when the breast rests on a substantially flat surface, the shell including a first opening allowing at least a portion of a nipple-areolar complex of the breast to protrude therethrough, and a first and second flange extending from the shell, the first and second flanges being configured to substantially secure the shell to the flat surface.

The shell may further comprise a third flange to secure the shell to a patient's chest wall. A first adhesive layer may also be included on the first, second and/or third flanges to secure the shell to the flat surface and/or a patient's chest wall. The shell may have a truncated generally semi-conical shape and may surround that portion of the breast not resting on the flat surface. The shell may include a substantially rigid outer member and a relatively softer inner member, the softer inner member, in use, being in contact with a patient's breast. A second adhesive layer may be disposed on the relatively softer inner member of the shell. The substantially rigid outer member may include a suction port and the relatively softer inner member may include a plurality of through holes in fluid communication with the suction port, to allow a patient's breast to be drawn toward the inner member when fluid is drawn from the suction port. The first opening may have a generally semi-circular shape and may include a first lip configured to allow at least one instrument to be clamped thereto. The shell may further include one or more second openings exposing the surface of the breast therethrough. A second lip may surround each second opening, to allow one or more instruments to be clamped thereto. The shell may include a plastic material.

The present invention may also be viewed as a method for imaging and biopsying a lesion in a breast, comprising the steps of:

compressing the breast between a first and a second compression plate;

localizing the lesion using mammography;

calculating spatial coordinates of the lesion;

inserting a biopsy device including an intra-tissue ultrasound transducer into the compressed breast and positioning the excisional device adjacent to the lesion using said spatial coordinates;

activating the intra-tissue ultrasound transducer and verifying correct placement of the biopsy device under ultrasonic guidance;

releasing the breast from compression by moving the first compression plate;

placing a breast stabilization device over the breast and securing the breast stabilization device at least to the second compression plate, and biopsying the lesion under ultrasonic guidance from the intra-tissue transducer of the excisional device.

The spatial coordinates may be calculated with respect to a peri-areolar border of the breast. The breast stabilization device may include an opening allowing at least a portion of a nipple-areolar complex to protrude therethrough and the biopsy device may be inserted near the peri-areolar border of the compressed and stabilized breast. The biopsying step may include a step of excising the lesion from the breast. A step of expanding the breast within the stabilization device prior to the biopsying step may also be carried out. The breast stabilization device may include a suction port and an inner member configured to contact the breast during use, the inner member including a plurality of through holes in fluid communication with the suction port, and the expanding step may include the step of drawing fluid from the suction port to cause the breast to be drawn toward the inner member. The first plate may be an upper plate and the second plate may be a lower plate. The securing step may include a clamping step to clamp the stabilization device to the second plate and/or an adhesion step to cause the stabilization device to adhere to the second plate. The securing step may include the step of securing the stabilization device to a patient's chest wall.

The present invention is also a method of imaging an uncompressed breast, comprising the steps of:

making an incision near a peri-areolar complex of the breast inserting a device including an ultrasound transducer through the incision and into the breast;

activating the ultrasound transducer within the breast, and imaging the breast using data returned from the ultrasound transducer on a display device.

The frequency of the ultrasound transducer may be selected within the range of about 7.5 MHz to about 20 MHz. A step of compressing the breast prior to the inserting step may also be carried out. A step of placing a breast stabilization device over at least a portion of the breast prior to the activating step may be carried out. The breast stabilization device may surround at least a superior portion of the breast.

According to another embodiment, a medical breast stabilization device according to the present invention comprises:

an outer member conforming generally to a shape of a superior portion of a female breast, the outer member including a suction port, and an inner member joined to the outer member and defining an interstitial space therebetween, the inner member being relatively softer than the outer member and comprising a plurality of through holes in fluid communication with the interstitial space and the suction port, the inner member being drawn in intimate contact with the patient's breast at least when fluid such as air or other gas is drawn from the suction port.

The outer and inner member may define an opening configured to allow at least a nipple-areolar complex of the breast to protrude therethrough. One or more flanges may be included to secure the stabilization device to a flat surface and/or to the patient's chest wall. One or more windows may be disposed through both the inner and outer members, the window or windows exposing a portion of the patient's breast therethrough. An adhesive layer may be disposed on the underside of the inner member, thereby causing the underside of the inner member to adhere to the patient's breast when the device is in use. The device may be a single use or multiple use device.

BRIEF DESCRIPTION OF THE DRAWINGS

For a further understanding of the objects and advantages of the present invention, reference should be made to the following detailed description, taken in conjunction with the accompanying figures, in which.

DESCRIPTION OF THE PREFERRED EMBODIMENTS

Scars along the border of the areola are much less noticeable than scars of similar length made in the side surface of the breast. The edge of the areolar complex is, therefore, an ideal point of entry into the breast, as compared with the side, top or bottom of the breast. However, conventional devices are designed to allow access to the interior of the breast only from the side of the breast and not from the areolar border. The present invention addresses these problems and facilitates access to the interior of a compressed and uncompressed breast around the peri-areolar complex.

Figure 1:
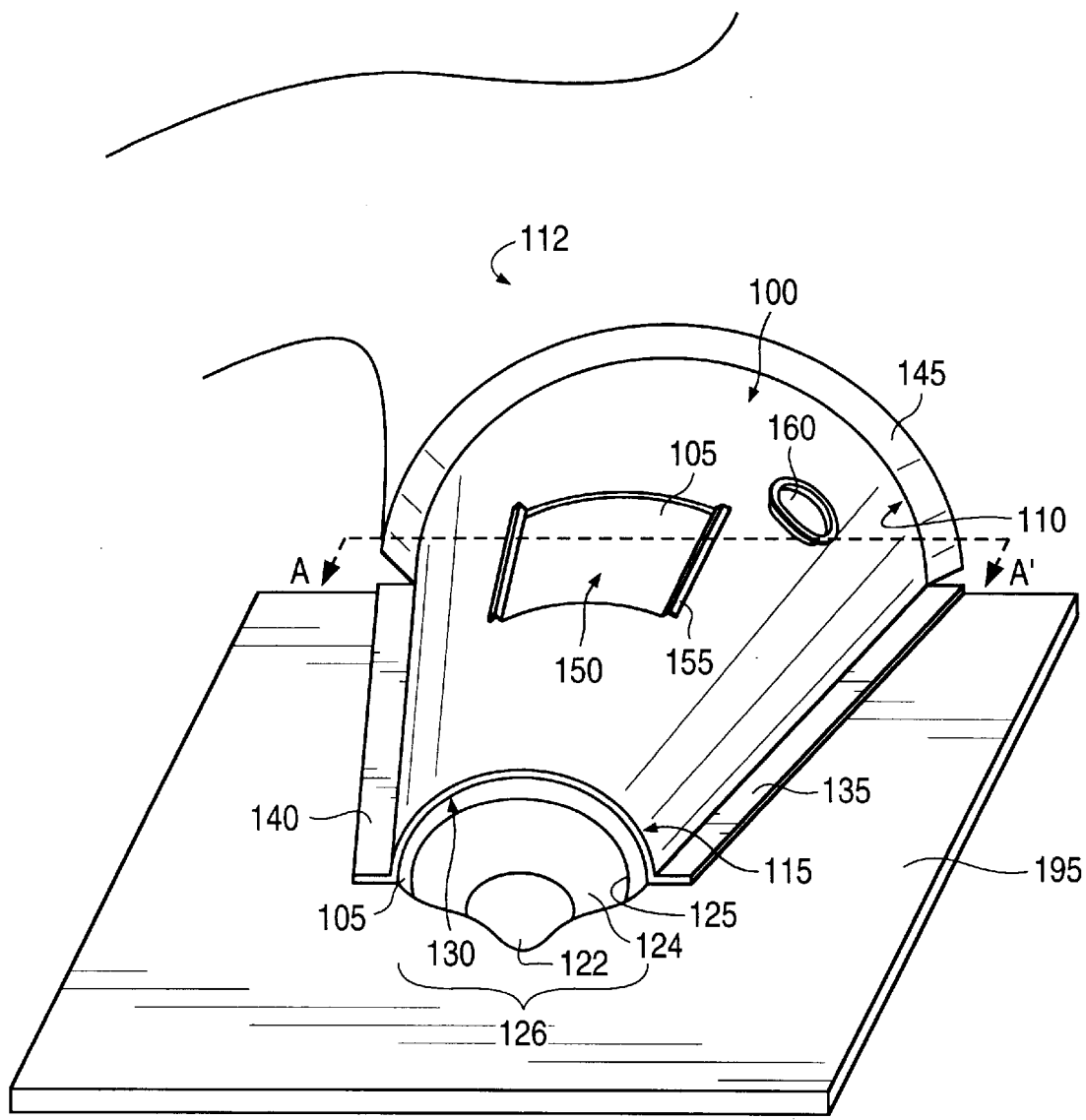
FIG. 1 shows a perspective view of a breast stabilization device in use, according to an embodiment of the present invention.

FIG. 1 shows an embodiment of the breast stabilization device according to an embodiment of the present invention. To better illustrate the functionality thereof, the breast stabilization device 100 shown in FIG. 1 is depicted in use, and secured to a flat surface 195. The flat surface 195, however, is shown for ease of description only and forms no part of the present invention. For example, the flat surface 195 may be a lower compression plate of a mammography imaging device (not shown). The breast stabilization device 100 has a shape that conforms to the superior and lateral sides of a female breast 105. This shape may, in general terms, be characterized as a truncated semi-conical shape, although the device's size and shape, according to the present invention, may be adapted to fit various breast sizes and shapes.

The breast stabilization device 100, according to the present invention, generally conforms to the size and shape of a female breast 105 as the breast 105 rests on a flat surface 195, such as a lower compression plate 195 of a mammography machine. Therefore, most of the inferior portion of the breast 105 shown in FIG. 1 lies substantially flat against the surface 195. For purposes of the present invention, the superior portion of the breast may be thought of that portion of the breast that is above a plane through the nipple and perpendicular to the chest wall and the inferior portion of the breast may be thought of that portion of the breast that lies below that plane, when the woman is in an upright position. Alternatively, the superior portion of the breast may be thought of as that portion of the breast that does not rest on the flat surface 195, irrespective of the position of the woman. The breast stabilization device 100 covers substantially the entire superior portion of the breast 105 as the breast 105 rests against the flat surface 100 and may cover some of the inferior portion thereof The breast stabilization device 100 includes a proximal end 110 and a distal end 115. The distal end 115 is disposed, in use, closest to the nipple-areolar complex 126 whereas the proximal end 110 of the breast stabilization device 100 is disposed, in use, closest to the patient's chest 112. The distal end of the device 100 is truncated, and includes an opening 130 that is configured to allow, in use, at least a portion of the nipple-areolar complex to protrude therethrough. Indeed, as shown in FIG. 1, the nipple 122 and the areola 124 protrude from the opening 130 of the breast stabilizing device 100 according to the present invention. Moreover, the opening 130 may allow a portion of the breast 105 that is adjacent the peri-areolar border 125 to be exposed therethrough.

The breast stabilization device 100 shown in FIG. 1 may also include a first flange 135 and a second flange 140. The first and second flanges 135, 140 may be disposed on either side of the breast stabilization device 100 and may extend parallel to the flat surface 195. The flanges 135 and 140 secure the breast stabilization device 100 to the flat surface 195. For example, the first and second flanges 135, 140 may include an adhesive layer on the side thereof facing (in use) the flat surface 195. Alternatively, the first and second flanges 135, 140 may be clamped to the flat surface 195 by any conventional clamping tool. Alternatively still, both an adhesive layer on the side of the flanges 135, 140 facing the flat surface 195 and clamping tool(s) may be employed to secure the breast stabilization device 100 to the flat surface 195. The flanges 135, 140 may extend all or a portion of the distance from the proximal end 110 of the device 100 to the distal end 115 thereof. The flanges 135, 140 may be continuous as shown in FIG. 1, or may be composed of a plurality of discrete elements facing the flat surface 195.

The breast stabilization device 100 may also include a third flange 145. The third flange 145 may be disposed at or near the proximate end 110 of the breast stabilization device 100 and may secure the device 100 to the patient's chest wall 112. Preferably, the side of the third flange 145 facing the patient's chest wall includes an adhesive layer to seal device 100 against the skin of the patient's chest. Whereas the first and second flanges 135, 140 may include relatively stiff material, such as a relatively hard plastic material for example, the third flange 145 may be relatively softer and include a relatively soft plastic material. In this manner, a good and substantially fluid (e.g., air)-tight seal may be formed between the proximal end 110 of the device 100 and the patient's chest wall 112.

The breast stabilizing device 100 may include one or more windows 150 (one such window 150 being shown in FIG. 1) exposing the breast 105 therethrough. The window or windows 150 may include one or more lips 155. The lip or lips 155 may serve as a platform on which to attach or clamp, for example, instruments such as imaging devices and the like. Indeed, surface ultrasound may be carried out through the window or windows 150 during an imaging and/or interventional procedure and the surface ultrasound device (not shown) may be secured to the lip or lips 155 of the window or windows 150. The lip or lips 155 may be integral to the window or windows 160 or may be removable therefrom. If removable, the lip or lips 155 may be friction-fitted to the shell of the breast stabilization device 100, in the manner discussed in detail with reference to FIG. 3 below. A suction port or ports 160 may also be disposed within the breast stabilization device 100. A syringe or other vacuum-inducing device may be attached, clamped or otherwise removably affixed to the suction port or ports 160 to create a partial vacuum within the breast stabilization device 100, in the manner disclosed relative to FIG. 2.

Figure 2:
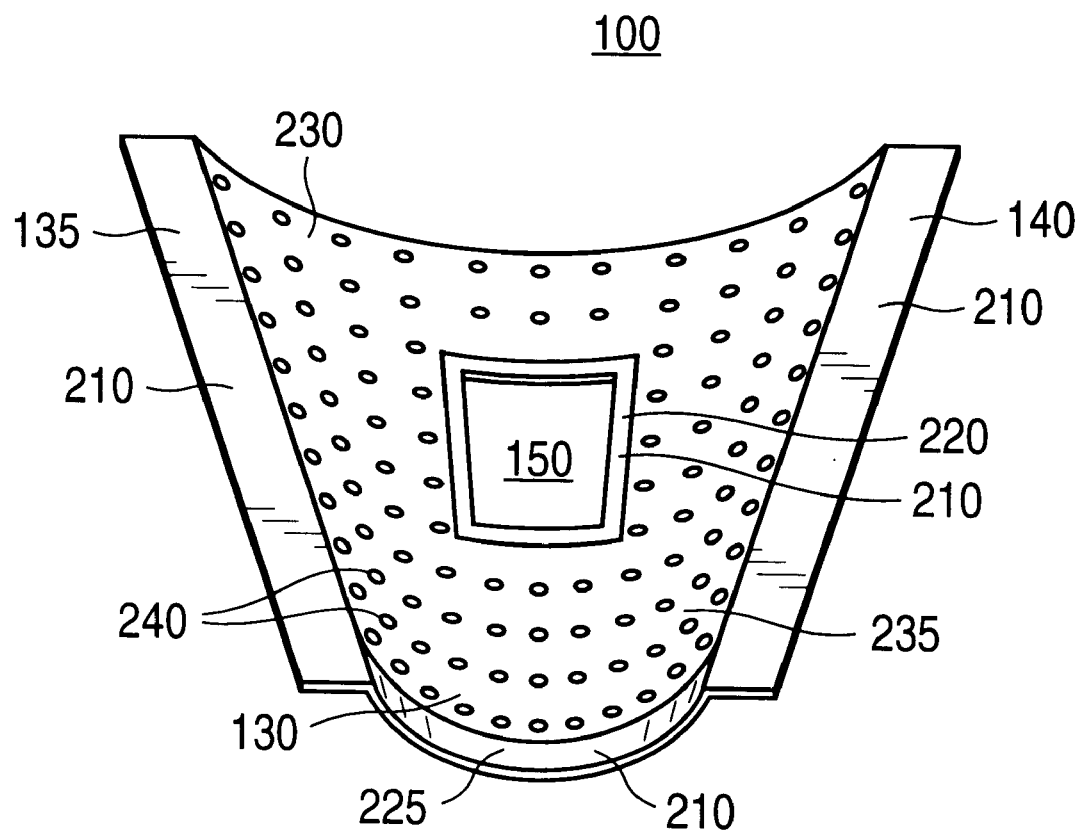
FIG. 2 shows a perspective view of the underside of a breast stabilization device, according to an embodiment of the present invention.

FIG. 2 shows the breast stabilization device 100 in an orientation wherein the underside 230 of the device 100 is visible, the underside being that side of the device 100 that comes into contact with the patient's skin (breast) during use. As discussed with reference to FIG. 1, a layer of adhesive 210 may be disposed on each of the first, second and third flanges 135, 140 and 145, respectively. The adhesive 210 disposed on the third flange 145 may be different than the adhesive 210 disposed on the flanges 135 and 140, as the adhesive 210 disposed on the third flange 145 contacts the patient's skin. A smooth sealing surface 220 may surround the window or windows 150. The sealing surface 220 facilitates the maintenance of a good seal between the breast 105 (not shown in FIG. 2) and the breast stabilization device 100. A similar sealing surface 225 may surround the opening 130, again to facilitate the maintenance of a seal between the patient's breast and the stabilization device 100. An adhesive layer 210 may be disposed on the sealing surfaces 220, 225.

The underside 230 of the stabilization device may include a plurality of through holes 240. The through holes 240 are in fluid communication with the suction port 160 shown in FIG. 1. When the breast stabilization device 100 is disposed on a patient's breast 105 as shown in FIG. 1 and fluid (air, for example) is drawn through the suction port 160, the breast 105 is drawn toward the underside 230 of the device 100, thereby somewhat expanding the breast 105 between the flat surface 195 and the underside 230 of the breast stabilization device 100. To promote a good seal between the breast 105 and the device 100, an adhesive layer 235 may be disposed on the underside 230 of the breast stabilization device 100. For example, prior to use, the surgeon may peel a protective plastic film (not shown) from the underside 230 of the device 100, thereby exposing the adhesive 235 in preparation of the placement of the device 100 on the patient's breast 105.

Figure 3:
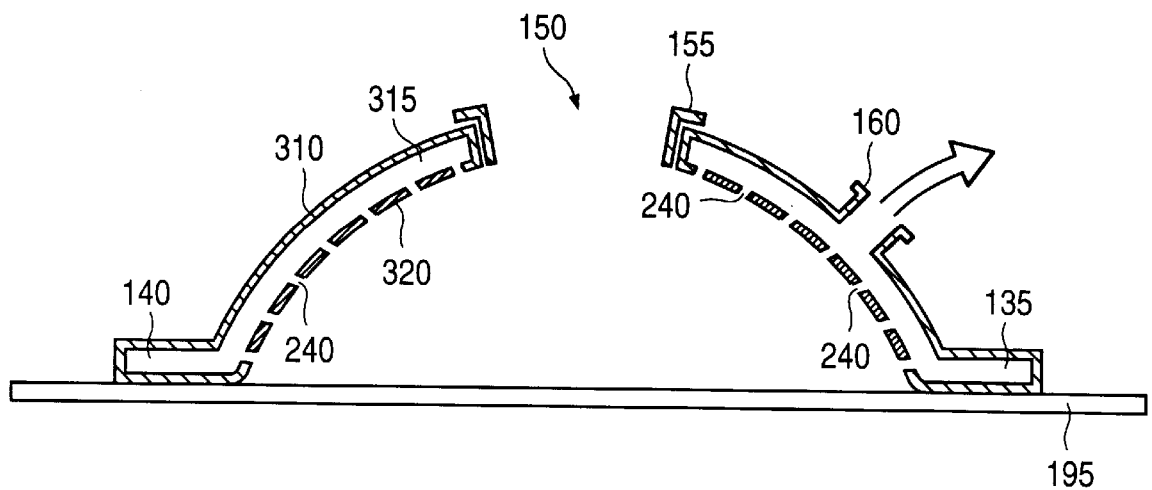
FIG. 3 is a cross-section of a breast stabilization device according to an embodiment of the present invention shown in FIG. 1, taken along line AA'.

FIG. 3 shows a cross-sectional view of an embodiment of the present invention, taken along line AA' of FIG. 1. As shown in FIG. 3, the breast stabilization device 100 may include an outer member 310 and an inner member 320. The outer member 310 and the inner member 320 may include a plastic material and may be joined to one another by an adhesive or by other means. The outer member 310 may be fabricated of a relatively stiff material and the inner member 320 may be of a relatively softer material, to better conform to the patient's breast 105 (shown in FIG. 1). The outer member 310 and the inner member 320 may be formed and joined to one another so as to create an interstitial space 315 therebetween. The inner member 320 may include a plurality of through holes 240 (FIG. 2), each of which being in fluid communication with the interstitial space 315 and the suction port 160. In this manner, after placement of the stabilization device 100 on the patient's breast 105, fluid, such as air, may be drawn from the suction port 160, thereby causing the breast 105 to be drawn toward the underside 230 of the stabilization device 100. This, in turn, may cause the breast 105 to expand somewhat within the device 100. The lip or lips 155 may be integral at least to the outer member 310 or may be removable and friction-fitted thereto, for example.

Figure 4:
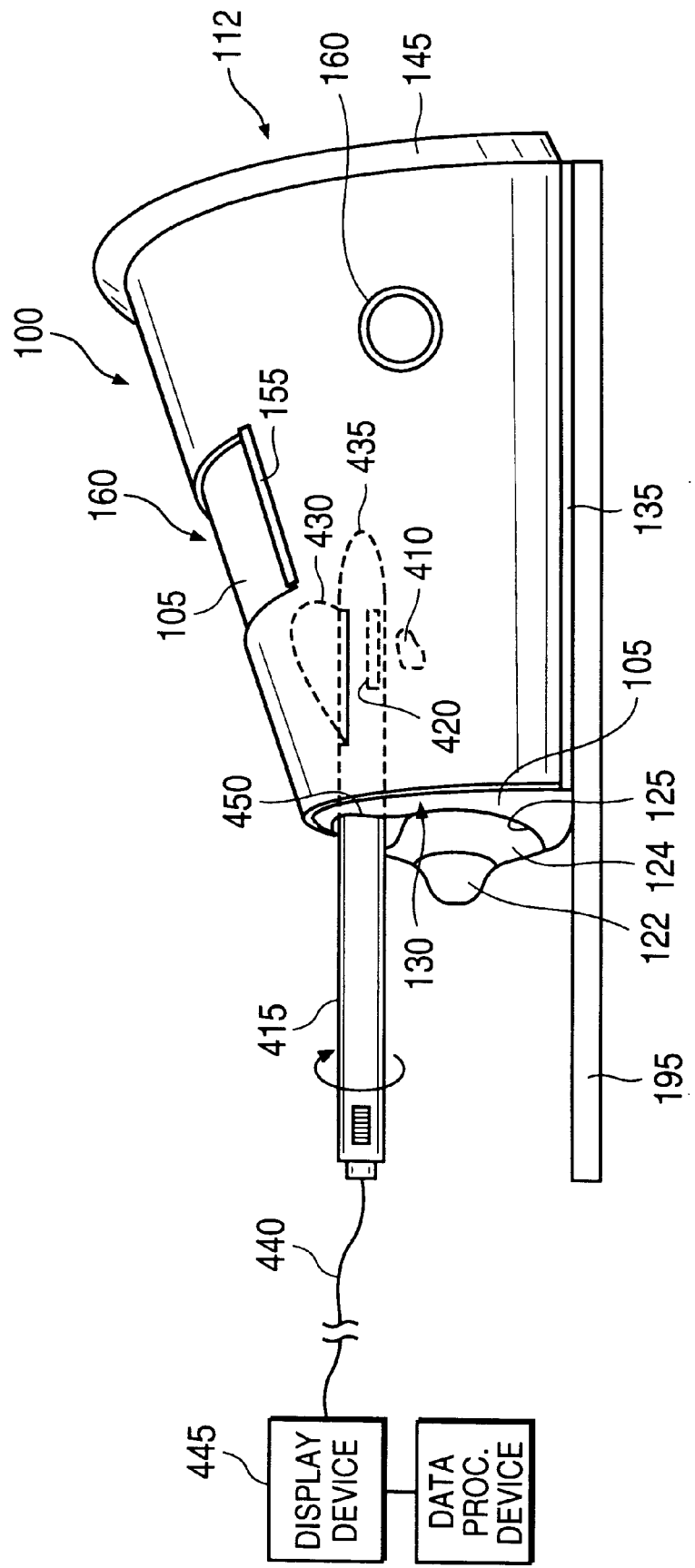
FIG. 4 is a side view of the breast stabilization device in use, according to an embodiment of the present invention, showing an interventional device inserted in the breast tissue.

FIG. 4 shows an embodiment of the present invention in use, during an imaging and interventional (e.g., biopsy or excisional) procedure. FIG. 4 is a side view (not to scale) of the stabilization device 100 disposed on a breast 105. The stabilization device 100 may be secured to a flat surface 195, such as a lower compression plate of a mammography device. The stabilization device 100 shown in FIG. 4 may also be secured to the patient's chest wall 112 by means of a preferably adhesive third flange 145. An imaging and/or interventional device 415 (not shown to scale in FIG. 4) is shown inserted into the breast 105. The device 415 is shown inserted through an incision 450 made in the peri-areolar border 125. For ease of reference, the portion of the device 415 that is inserted in the breast 105 is shown in dashed lines. As shown, the device 415 is inserted through the opening 130 of the device 100, in the incision 450 in the breast 105 and guided adjacent to a lesion 410, such as a group of suspicious cells, microcalcifications, necrotic cells or cancer. The imaging and/or interventional device 415 is preferably equipped with an ultrasound transducer 420. Once the device 415 is correctly positioned near the lesion 410, the ultrasound transducer 420 may be activated to generate information regarding the structure of the breast 105 from within the breast tissue itself The frequency of the ultrasound transducer 420 may be selected within the range of about 7.5 MHz to about 20 MHz. The information generated by the ultrasound transducer 420 may be relayed via a communication link 440 (wired or wireless) to a display and/or data processing device 445, preferably located within the view of the operator of the device 415. In this manner, the device 415 constitutes an intra-tissue ultrasonic device that penetrates directly into breast tissue to image structure therein. For example, a suitable imaging/interventional device 415 is described in commonly assigned United States patent application Ser. No. 09/146,743, entitled "Excisional Biopsy Devices And Methods", filed on Sep. 3, 1998, the disclosure of which is hereby incorporated by reference in its entirety.

As shown in FIG. 4, the device 415 may also be equipped with a cutting tool 430 which may utilize a sharpened edge and/or RF energy to cut and/or cauterize the breast tissue. Advantageously, the intra-tissue ultrasound transducer 420 allows real time imaging of the lesion 410 within the breast 105 as the device 415 is deployed within the breast adjacent the lesion 410. This real time imaging allows a precise deployment of the cutting tool 430 to only cut that which is strictly necessary to obtain the necessary tissue sample and/or to excise the lesion in toto. The intra-tissue ultrasound transducer may also be advantageously utilized to insure that adequate margins of healthy tissue are present around the excised lesion 410, both to reduce the probability of seeding the retraction path of the device 415 with potentially cancerous cells and to allow a proper histopathological examination of the entire lesion 410.

Figure 5:
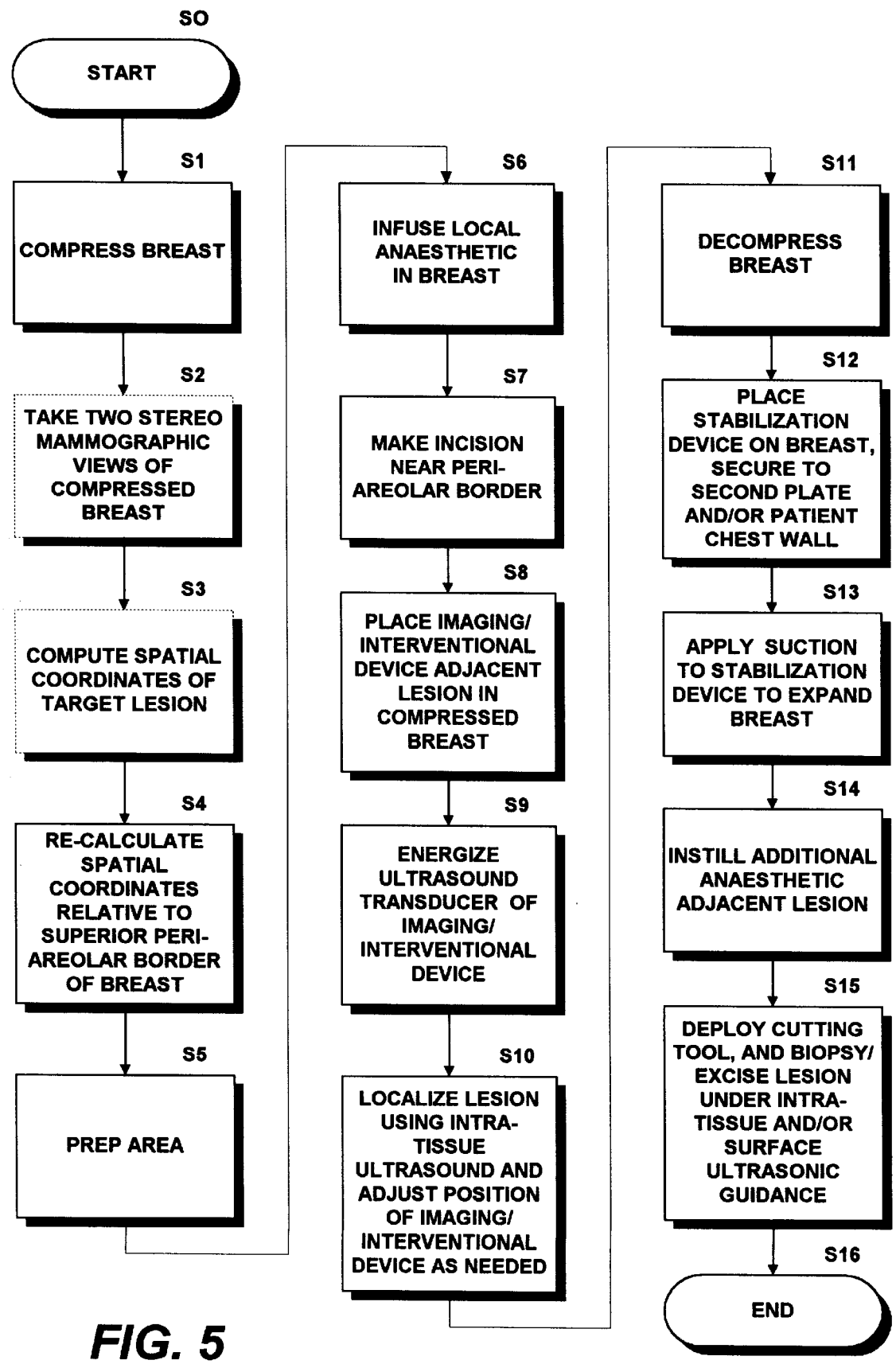
FIG. 5 is a flow chart of a method of biopsying and/or excising a breast lesion according to an embodiment of the present invention.

FIG. 5 is a flowchart of a method of biopsying and/or excising a breast lesion according to an embodiment of the present invention. The method begins at step S0. At Step S1, the breast is compressed, e.g., between a first flat surface and a second flat surface. For example, the first flat surface may include an upper compression plate of a mammography device and the second flat surface may include a lower compression plate thereof In step S2, at least two stereo mammography views are taken of the compressed breast. Step S3 calls for the computation, from the stereo views, of the spatial coordinates (for example, x, y, z rectangular coordinates) of the target lesion within the breast, such as is shown at reference numeral 410 in FIG. 4. Steps S2 and S3 are optional, as indicated by the dashed lines, it being possible to use standard mammography localization techniques. In step S4, the spatial coordinates computed in S3 are re-calculated, so that the coordinates indicate the position of the lesion within the breast relative to the superior peri-areolar border of the breast, as shown at 450 in FIG. 4. In step S5, the area (e.g., the nipple-areolar complex 126 shown in FIG. 1) is surgically prepped with, for example, Betadine. Local anaesthetic is infused in the breast in step S6 and an incision is made at or near the peri-areolar border, as shown at 450 in FIG. 4.

In step S8, an imaging and/or interventional device, such as shown at 415 in FIG. 4, is inserted through the incision made in step S7 and the device is advanced through the breast to a position adjacent the target lesion in the compressed breast. Step S8 is preferably carried out under stereotactic guidance to the re-calculated spatial coordinates obtained in step S4. The position of the imaging/interventional device may be confirmed using mammography. At step S9, the ultrasound transducer of the imaging/interventional device is energized. An embodiment of a suitable imaging/interventional device is shown at reference 420 in FIG. 4. Using at least such intra-tissue ultrasound, the lesion is identified and localized and the imaging/interventional device is precisely positioned relative to the lesion within the compressed breast.

Steps S11 through S16 are carried out on an uncompressed breast. In step S11, the breast is decompressed. For example, the upper compression plate of the mammography device may be moved and/or removed, thus allowing the breast to decompress. In step S12, the breast stabilization device according to the present invention, such as shown at 100 in FIG. 1, is fitted over the breast, while the breast rests on the second flat surface, such as the lower compression plate of the mammography device. The stabilization device is then secured to the second flat surface and/or to the patient's chest wall. It is important that the patient remain substantially immobile during and after step SI I as the breast is decompressed. In step SI 3, suction is applied to the stabilization device according to the present invention through, for example, the suction port 160 shown in FIGS. 1, 3 and 4. This causes fluid (air, for example) to be drawn through the plurality of through holes 240 of FIG. 2, through the interstitial space 315 between the outer member 310 and the inner member 320 of FIG. 3 and through the suction port 160. This draws the breast 105 in intimate contact with the underside 230 of the stabilization device 230, slightly expanding the breast volume and stabilizing the breast 105 within the device 100.

In step S14, additional anaesthetic is infused within the breast as needed. Finally, in step S15, the cutting tool, such as the cutting tool shown at 430 in FIG. 4 is deployed and the lesion is biopsied and/or excised under the guidance of the preferably real time intra-tissue images of the breast generated by the imaging/interventional device ultrasound transducer. Alternatively, the cutting tool may be deployed under both intra-tissue ultrasound as described above and under surface ultrasound, from the window or windows 150 shown in FIGS. 1–4. The tissue sample or lesion may then be biopsied or excised and retrieved from the imaging/interventional device, the device retracted and the incision closed. The method ends at step S16.

While the foregoing detailed description has described several embodiments of this invention, it is to be understood that the above description is illustrative only and not limiting of the disclosed invention. For example, the number and shape of the windows and suction ports may differ from that illustrated and described herein, without, however, departing from the spirit and scope of the present invention. A number of other modifications will no doubt occur to persons of skill in this art. All such modifications, however, should be deemed to fall within the scope of the present invention. Thus, the invention is to be limited only by the claims as set forth below.

What is claimed is:

1. A breast stabilization device for imaging and invasive medical procedures, comprising:
    a shell configured to surround a portion of a breast when the breast rests on a substantially flat surface, the shell including a first opening allowing at least a portion of a nipple-areolar complex of the breast to protrude therethrough, and
    a first and second flange extending from the shell, the first and second flanges being configured to substantially secure the shell to the flat surface.

2. The device of claim 1, wherein the shell further comprises a third flange, the third flange being configured to substantially secure the shell to a patient's chest wall.

3. The device of claim 1, further comprising a first adhesive layer, the first adhesive layer being disposed on at least one of the first, second and third flanges to substantially secure the shell to at least one of the flat surface and a patient's chest wall.

4. The device of claim 1, wherein the shell has a truncated generally semi-conical shape that surrounds that portion of the breast not resting on the flat surface.

5. The device of claim 1, wherein the shell includes a substantially rigid outer member and a relatively softer inner member, the softer inner member, in use, being in contact with a patient's breast.

6. The device of claim 5, further comprising a second adhesive layer, the second adhesive layer being disposed on the relatively softer inner member of the shell.

7. The device of claim 5, wherein the substantially rigid outer member includes a suction port and wherein the relatively softer inner member includes a plurality of through holes in fluid communication with the suction port, to allow a patient's breast to be drawn toward the inner member when fluid is drawn from the suction port.

8. The device of claim 1, wherein the first opening has a generally semi-circular shape.

9. The device of claim 1, wherein the first opening includes a first lip configured to allow at least one instrument to be clamped thereto.

10. The device of claim 9, wherein the first lip is removable.

11. The device of claim 1, wherein the shell further includes at least one second opening, said at least one second opening exposing a surface of the breast therethrough.

12. The device of claim 11, further comprising a second lip surrounding each said at least one second opening, the second lip being configured to allow at least one instrument to be clamped thereto.

13. The device of claim 10, wherein the second lip is removable.

14. The device of claim 1, wherein the shell includes a plastic material.

15. A medical breast stabilization device, comprising:
    an outer member conforming generally to a shape of a superior portion of an uncompressed female breast, the outer member including a suction port;
    an inner member joined to the outer member and defining an interstitial space therebetween, the inner member being relatively softer than the outer member and comprising a plurality of through holes in fluid communication with the interstitial space and the suction port, the inner member being drawn in intimate contact with the patient's breast at least when fluid is drawn from the suction port.

16. The device of claim 15, wherein the outer and inner member define an opening configured to allow at least a nipple-areolar complex of the breast to protrude therethrough.

17. The device of claim 15, further comprising at least one flange, said at least one flange securing the stabilization device to at least one of a flat surface and to a chest wall of the patient.

18. The device of claim 15, further comprising at least one window through both the inner and outer members, said at least one window exposing a portion of the patient's breast therethrough.

19. The device of claim 15, wherein an adhesive layer is disposed on an underside of the inner member, thereby causing the underside of the inner member to adhere to the patient's breast when the device is in use.

20. The device of claim 15, wherein the device is a single use device.

21. The device of claim 15, wherein the device is a multiple use device.

22. The device of claim 15, wherein the fluid includes air.

* * * * *